(12) United States Patent
Wang

(10) Patent No.: US 9,414,905 B2
(45) Date of Patent: Aug. 16, 2016

(54) MUSCLE PROSTHESIS WITH SUSPENSION FIXING APPARATUS FOR IMPLANTATION IN HUMAN BODY AND PRODUCTION METHOD THEREOF

(76) Inventor: Jiangning Wang, Beijing (CN)

( * ) Notice: Subject to any disclaimer, the term of this patent is extended or adjusted under 35 U.S.C. 154(b) by 322 days.

(21) Appl. No.: 13/980,020

(22) PCT Filed: Jan. 16, 2012

(86) PCT No.: PCT/CN2012/070386
§ 371 (c)(1),
(2), (4) Date: Sep. 25, 2013

(87) PCT Pub. No.: WO2012/097711
PCT Pub. Date: Jul. 26, 2012

(65) Prior Publication Data
US 2014/0018918 A1 Jan. 16, 2014

(30) Foreign Application Priority Data

Jan. 17, 2011 (CN) .......................... 2011 2 0012524

(51) Int. Cl.
*A61F 2/08* (2006.01)

(52) U.S. Cl.
CPC ........... *A61F 2/08* (2013.01); *A61F 2002/0894* (2013.01)

(58) Field of Classification Search
CPC .............................. A61F 2/08; A61L 2430/30
USPC ........................................... 623/13.11–14.13
See application file for complete search history.

(56) References Cited

U.S. PATENT DOCUMENTS

| 3,882,551 | A | 5/1975 | Helmer et al. |
| 4,584,722 | A | 4/1986 | Levy et al. |
| 6,214,047 | B1* | 4/2001 | Melvin ..................... A61F 2/08 623/11.11 |
| 6,592,623 | B1* | 7/2003 | Bowlin ..................... A61F 2/08 623/13.17 |

(Continued)

FOREIGN PATENT DOCUMENTS

| CN | 101850551 A | 10/2010 |
| CN | 202036367 U | 11/2011 |
| EP | 0614650 A2 | 9/1994 |

OTHER PUBLICATIONS

ISA China, International Search Report of PCT/CN2012/070386, State Intellectual Property Office of China, Apr. 19, 2012, 6 pages.

(Continued)

*Primary Examiner* — Suzette J Gherbi
(74) *Attorney, Agent, or Firm* — Alleman Hall McCoy Russell & Tuttle LLP

(57) ABSTRACT

A muscle prosthesis with a suspension fixing apparatus for implantation into a human body and production method thereof; the muscle prosthesis comprises a muscle prosthesis main body and the suspension fixing apparatus; the suspension fixing apparatus consists of at least one stretchable part and at least two fasteners; the suspension fixing apparatus can fix the muscle prosthesis to a human bone or human muscle tendon and fascia. The suspension fixing system can change the thickness and outer shape of the prosthesis according to the direction and intensity of a tensile force, thus satisfying the requirements of different body parts and different muscle thicknesses. Use of the suspension fixing apparatus allows the prosthesis to be fixed firmly and be structurally stable, thus solving the technical problem of drooping and shifting prostheses.

15 Claims, 6 Drawing Sheets

(56) References Cited

U.S. PATENT DOCUMENTS

| | | | |
|---|---|---|---|
| 7,715,918 B2* | 5/2010 | Melvin | A61N 1/3785 607/35 |
| 2002/0026794 A1 | 3/2002 | Shahinpoor et al. | |
| 2006/0287720 A1 | 12/2006 | Tse | |
| 2008/0217820 A1* | 9/2008 | Yost | B29C 47/0023 264/473 |
| 2009/0069902 A1* | 3/2009 | Tozzi | A61F 2/2481 623/23.72 |
| 2009/0192347 A1* | 7/2009 | Davila | A61B 17/06109 600/37 |
| 2010/0221301 A1* | 9/2010 | Le Visage | A61L 27/20 424/422 |
| 2010/0221303 A1* | 9/2010 | Le Visage | A61L 27/20 424/423 |
| 2012/0109166 A1* | 5/2012 | Melvin | A61F 2/0811 606/151 |
| 2012/0116505 A1* | 5/2012 | Shahinpoor | A61F 2/147 623/4.1 |
| 2013/0150977 A1* | 6/2013 | Gabriel | A61F 2/3859 623/20.32 |
| 2013/0274545 A1* | 10/2013 | Jenkins | A61F 2/0045 600/30 |
| 2014/0179990 A1* | 6/2014 | Davila | A61B 17/06109 600/37 |
| 2014/0350676 A1* | 11/2014 | Melvin | A61F 2/0811 623/13.14 |
| 2015/0337874 A1* | 11/2015 | Park | F15B 15/103 92/5 R |

OTHER PUBLICATIONS

International Bureau of WIPO, International Preliminary Report of PCT/CN2012/070386, Switzerland, Jul. 17, 2013, 15 pages.

* cited by examiner

MUSCLE PROSTHESIS WITH SUSPENSION FIXING APPARATUS FOR IMPLANTATION IN HUMAN BODY AND PRODUCTION METHOD THEREOF

TECHNICAL FIELD

This invention generally relates to a reshaping product in the medical field, more particularly to a kind of muscle prosthesis with suspension fixing device for implantation into a human body. The muscle prosthesis can be used to fill in soft tissue defects and the thickening of thin and small limbs (that is, padding), The muscle prosthesis has good elasticity and can fasten a certain joint to a certain functional position, and replaces the paralyzed muscle to exert part of its functions; in addition, the muscle prosthesis of this invention can also bulge defects and umbilicated soft tissues, and actually play a aesthetic role.

BACKGROUND TECHNOLOGY

With the continuous development of medical treatment and plastic surgery, prosthesis implantation has become an ideal operation method to thicken limbs. However, with existing technology, the muscle prosthesis implanted into various parts of human body is not fastened with additional fixing device, thus, with the frequent movement of limbs prosthesis displacement often causes, as a result, the appearance of the prosthesis implantation part shall be changed, and even cause prosthesis tearing because of strenuous exercise and the weight of prosthesis itself, etc. Prosthesis displacement: when prosthesis is implanted into a human body, the natural tissues of the human body shall form an envelope around the prosthesis, with prolongation of time, the prosthesis envelope capsule may become wider and bigger, causing prosthesis displacement. Prosthesis fracture: fracture shall easily occur to prosthesis under the effect of extrusion and shearing force. Although through the use of high-viscosity gel materials at present, the silica gel shall not flow away when fracture occurs, damages to the natural tissues around the muscle prosthesis may occur, so that leading to complication.

INVENTION CONTENTS

One of the purposes of the invention is to provide a kind of muscle prosthesis with suspension fixing device for implantation into a human body, and the muscle prosthesis is fastened to the skeletons of human body by the fixing and tensile members, to solve the prosthesis displacement, prosthesis fracture and other problems caused because of frequent movement of limbs and the weight of prosthesis itself, therefore, it is favour of the prosthesis to exist in human body for a long term.

Another purpose of the invention is to provide a manufacturing method for the muscle prosthesis with suspension fixing device for implantation into a human body.

The purposes of the invention can be realized by the following technical proposal:

The invention provides a kind of muscle prosthesis with suspension fixing device for implantation into a human body, the muscle prosthesis includes: muscle prosthesis main body and suspension fixing device. The suspension fixing device is consisted of at least one tensile member and at least two fixing members, the tensile member is inbuilt in the muscle prosthesis main body and is extended to outside of the main body, and the fixing member is connected with the extending end of the tensile member, so that the suspension fixing device can fasten the muscle prosthesis to the skeletons of human body or muscle tendon and fascia of human body.

In an preferred embodiment of the invention, the muscle prosthesis main body includes silicon external capsule and filler, the filler is filled in the silicon external capsule and integrally formed with the external silicon capsule. The tensile member is arranged to be several pull lines which are inbuilt in the silicon external capsule in both longitudinal and lateral directions and form net sling structure together with silicon external capsule and all of the longitudinal and lateral pull lines crookedly run (including polyline shape and curve line shape); the fixing member is connected to the pull line, and the suspension fixing device consisted of fixing member and pull line can elastically fasten the muscle prosthesis to the skeletons.

In another preferred embodiment of the invention, the muscle prosthesis main body is solid colloidal silica, and the tensile members impenetrate the solid colloidal silica longitudinally and/or laterally.

The invention also provides a manufacturing method for the muscle prosthesis with suspension fixing device for implantation into a human body, characterized in that, the manufacturing method includes: setting muscle prosthesis main body and suspension fixing device consisted of at least one tensile member and at least two fixing members; embedding the tensile member into the main body of the muscle prosthesis so that the tensile member can extend to the outside of the main body of the muscle prosthesis; connecting the fixing member to extending end of the tensile member, and fastening the muscle prosthesis to the skeletons of human body or muscle tendon and fascia of human body by the fixing member and the tensile members.

Compared with existing technologies, the invention has the following beneficial technical effects:

1. One of the key points for the invention is the suspension fixing device of prosthesis. When compared with prosthesis in existing technologies, which often occurs ptosis and displacement as the prosthesis does not have suspension fixing device, and often brings inconveniences to clinical application and increases complications of prosthesis implantation, in the invention, the prosthesis is firmly fastened, and its structure is stable, as such this invention solves the problems of prosthesis ptosis and displacement.

2. The invention designs a braided fabric of pull line that is packed together with weaving package of silicon external capsule and runs in S direction. For example, when we adjust the longitudinal pull line that extends outside of the lumbricals prosthesis, we can fasten the metacarpophalangeal joint to the functional position of hand, thus, the prosthesis shall have the functions of elastically fastening joint, reducing the preparations before implantation, and effectively changing the shape of muscle prosthesis by rivet or similar fixing member stretching pull line, thus, greatly simplifying the following implantation operation process.

3. The invention extends the longitudinal and lateral pull lines of to outside of the prosthesis, and the prosthesis thickness and contour can be changed according to the direction and strength of the pull force, thus, satisfying the requirements of muscle at different positions and of different thickness. For example: when repairing temporalis, we can make a circular muscle prosthesis, and adjust it to suitable shape by stretching the surrounding pull lines. When repairing gluteus maximus and gluteus medius, by stretching pull lines extend to outside of the prosthesis, we can adjust it into the sector shape or leaf shape, etc.

4. The invention can manufacture muscles prosthesis for various positions of human body, for example, lumbricals and interosseus of hand. The invention has the advantages of wide application range and vast prospects for popularization and application.

5. The invention can bulge defects and umbilicated soft tissues, and actually play the function to improve the aesthetic effect of human body.

DETAILED DESCRIPTION

Figure 1:
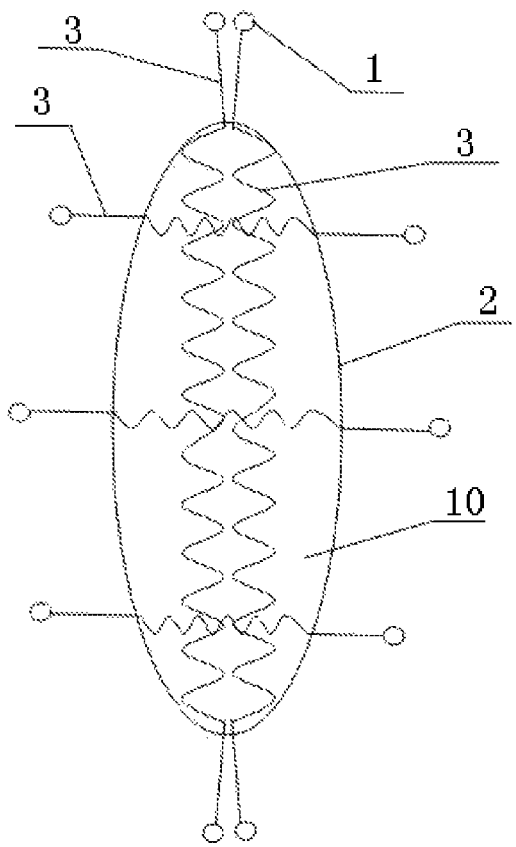
FIG. 1 is the front view of a muscle prosthesis according to the invention.
Figure 2:
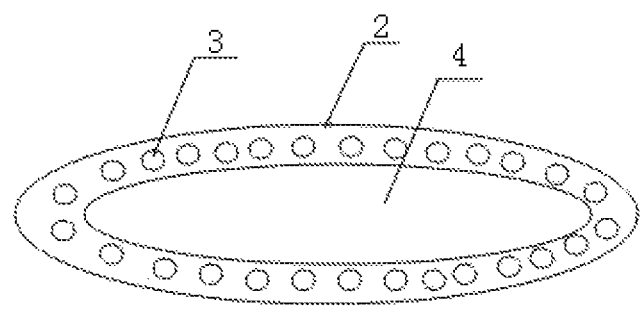
FIG. 2 is cross section structure diagram of the muscle prosthesis according to the invention.

Specific embodiments of the invention are described in detailed thereinafter with reference to FIGS. 1-10. FIG. 1 is the front view of a muscle prosthesis according to the invention, FIG. 2 is cross section structure diagram of the muscle prosthesis according to the invention, in which, 10 expresses muscle prosthesis main body, 1 expresses the fixing member (rivet, etc.), 2 expresses silicon external capsule, 3 is the stretching member (pull line, etc.), 4 expresses the filler. In FIGS. 1-9, the same members/components are represented with the same reference numbers.

The invention provides a kind of muscle prosthesis implanted into human body, the muscle prosthesis includes: muscle prosthesis main body and suspension fixing device. The suspension fixing device is consisted of at least one tensile member and at least two fixing members, the tensile member is inbuilt in the muscle prosthesis main body and is extended to the outside of the muscle prosthesis main body, and the fixing member is connected with a extending end of the tensile member, so that the suspension fixing device can fasten the muscle prosthesis to the skeletons of human body or muscle tendon and fascia of human body. When compared with prosthesis in existing technologies which often occurs ptosis and displacement and often bring in a lot of inconveniences to clinical application and increases complications of prosthesis implantation, in the invention, the muscle prosthesis is firmly fastened by adopting the suspension fixing device, and the structure is stable, this invention solves the problems of muscle prosthesis ptosis and displacement.

In the invention, the fixing member fastens the stretching member to the skeleton or muscle tendon and fascia of human body, and shape of the muscle prosthesis main body is changed by stretching the tensile members in different directions with different forces by the fixing member, thereby, the muscle prosthesis main body shall match with a space in which the muscle prosthesis will be implanted.

FIG. 1 is the front view of the muscle prosthesis according to the invention. In present embodiment, the muscle prosthesis can be used in the quadriceps muscle, the muscle prosthesis main body 10 of the present invention comprises a silicon outer bag 2 and the filler 4, the filler 4 is filled in the outer bag 2 and is integrally formed with the outer bag 2. The tensile member 3 is set as multiple of pill lines 3, the multiple of pill lines 3 are buried in the silicon outer capsule 2 in both longitudinal and lateral directions and combine with the silicon outer bag 2 to form net sling structure, and run crookedly in the longitudinal and transverse directions, In the present invention, the crooked running including polygonal line shape and curved shape; Fixing member 1 connected to the pull line 3, suspension fixing device marked up by the fixing member 1 and the pull lines 3 can elastically fix a muscle prosthesis to the bone. Because the silicon outer capsule is flexible and pull lines run crookedly, and form a whole with silicon external capsule. At this time pull lines being bending state, pull line can be straightened by stretching the pull line, after release of tensile stress, the pull line can rebound, so that the prosthesis can achieve elastic contraction, the pull line exposed to the outside of silicon outer capsule can serve the function of replacing of the tendon, after stretching properly, the pull lines exposed outside the silicon outer capsule 2 are fixed via the fixing members 1 to upper and lower start and stop points of human body natural muscles which are replaced by prosthesis, that is, fixed to the bones in the human body. It should be noted that, in order to reduce the complexity of operations while to ensure prosthesis be properly fixed on the joints, a portion of pull lines 3 has fixing member 1; and the other portion of pull lines 3 does not.

Preferably, tension lines 3 run along S shape in both longitudinal and lateral directions; Further more, each of tension lines 3 runs in S shape in which S is formed by two semicircles having same radius, and comply with such principles, that is, tension lines 3 knot at intersections between longitudinal and lateral directions, a longitudinal tension line 3 does not intersect with a longitudinal tension line 3, a lateral tension line 3 does not intersect with a lateral tension line 3, to form net sling-like knitting. Thus, not only stretching length of each tension wire can be calculated easily, but also can make the muscles prosthesis stress uniformly when stretching. Further based on the size of the muscle prosthesis, the size of space into which the prosthesis will be implanted, anatomic structure of a joint around the implanted prosthesis, the prosthesis will be fixed to joints properly, thereby greatly reducing the preparatory work before implantation to facilitate subsequent implant operation.

In the present embodiment, the tension wire material can be ultrahigh molecular weight polyethylene and nylon composite cord. BOSS mechanical stretching machine U.S. experiment proves, each pull cord can withstand 25 pounds of tension, fatigue experiment proves that its service life can reach 45 years. If each pull cord runs in S shape in which S is formed by two semicircles with radius of 2.5 mm, and is arranged following the principles of knotting at intersections of longitudinal and lateral tension lines, of no intersection between the longitudinal tension lines, of no intersection between the lateral tension lines, according to the arc length formula $L=n\pi R/180$, Where n is the arc angle, R is the radius, then $L=180°\times\pi\times2.5/180°=7.85$ mm. When the tension wires are fully extended, they form a net composed of a plurality of rectangular mesh, length and width are equal in each of the rectangular mesh, its side length equal to the arc length H=7.85 mm, its circumference is Z=31.42 mm, so that elastically extensible length value of each semicircle can be calculated as TXZ=H−2R=7.85 mm−5 mm=2.85 mm.

Wherein the radius of the semicircle is determined based on patient's missing muscle portion sizes, the standard is that silicon outer bag 2 can be stretched as two times length as the length of its nature, The tension wire 3 can be stretched less than three-fifths of the stretchable length of the outer capsule. Specifically, the outer capsule 2 is silica gel organic compounds, and has good flexibility, the elastic stretchable length of which can be as twice length as the natural length, That is, if the silicon outer bag 2 is a natural length of 10 cm it can be stretched to 20 cm. Stretchable length of the tension wire 3 can be less than three-fifths of the stretchable length of the outer capsule (initially, length of S-shaped tensile line is a straight line distance from its start point to end point). Whereby Stretching tension lines 3 change the shape of the muscle prosthesis more conveniently and flexibly from different directions and at different intensity (i.e, the tension wire along with the silicon outer capsule stretches tension lines from different directions to change the shape of the silicon outer capsule), thus the muscle prosthesis matches with the implantable space to maximize original function of the muscles of the defect. And it is not necessary to precisely tailor muscle prosthesis, the shape of a muscle prosthesis can be changed based on general shape and volume of the prosthesis to match well the space in which the prosthesis will be implanted. The United States BOSS mechanical tensile machine experiment proves that the silicon outer capsule 2 can withstand stretching over five million times without distortion, cracking, or damage.

In another embodiment of the present invention, the tension wires 3 run along V-shape in the longitudinal and transverse directions, following the principles of knotting at intersections of the longitudinal and transverse tension wires 3, of no intersection between the longitudinal tension wires 3, of no intersection between the transverse tension wires 3. However, the present invention is not limited to this, tension wire 3 can run in longitudinal and transverse directions, and may be polygonal line or varieties of curve lines, as long as they reach a position elasticity fixed the muscle prosthesis to a bone, that can realize the entire prosthesis elastically stretchable function. It need note that the tension wire 3 may be laid in a straight line shape, this will be specifically described thereinafter.

Preferably Filler 4 can be high viscoelastic silicone gel, boron body or various other flexible materials which can be suitable for implantation in human body.

Preferably, the tensile member 3 may be elastic member, for example, one or more of elastic pull line (such as ultra-high molecular polyethylene and nylon composite wire), elastic cloth, and polyporous elastic cloth or a combination thereof may be used. However, the material is not limited to this; other known medical materials which could be safely implanted into the human body could be used as long as they have a certain degree of tenacity and retractility.

Figure 8:
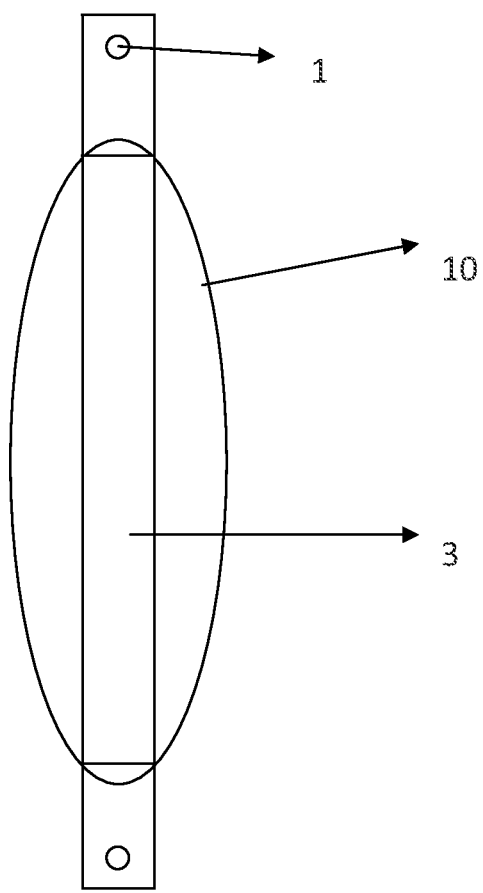
FIG. 8 is a schematic diagram of an embodiment of tensile member laid along straight line in the silicon external capsule according to the invention.

In another embodiment of present invention as shown in FIG. 8, a stretching member according to the invention is laid in a solid colloidal silica along straight line. Stretching member 3 impenetates the muscle prosthesis main body in the longitudinal and/or transverse direction and combines with the main body, and runs along straight line in the longitudinal and/or transverse direction. Fixing member 1 connects to the stretching member 3; suspension fixing device composed of fixing member 1 and stretching member 3 can fasten muscle prosthesis to the bone or human tendons and fascia, functions fastening the muscle prosthesis, has stable construture to prevent displacement and rupture of the muscle prosthesis, thus contributing to the long-term presence in the human body. In the present embodiment, the tensile member 3 may be made of metal sheet, but does not limited thereto; the tensile member 3 can be made of other elastic or non-elastic material which have a certain degree of strength.

Figure 9:
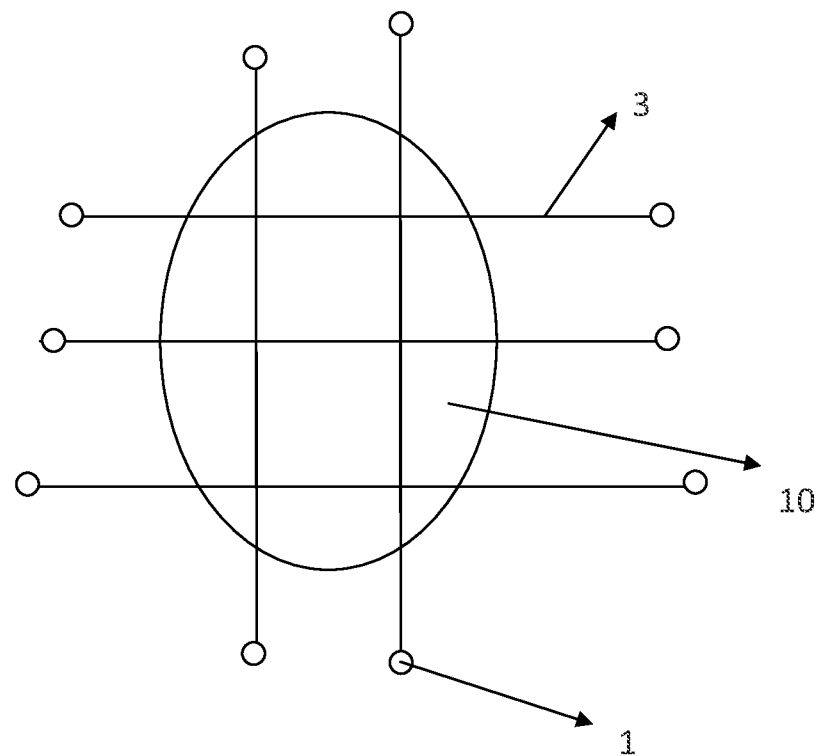
FIG. 9 is a schematic diagram of an embodiment of tensile member laid along straight line in the solid colloidal silica according to the invention.

In another embodiment of the present invention as shown in FIG. 9, tensile member according the invention is laid in the solid colloidal silica along a line. Muscle prosthesis part 10 is a solid silicone; tensile member impenetrates the solid colloidal silica in the longitudinal and/or transverse direction. In this embodiment, the stretching member 3 is elastic pull wires (such as ultra high molecular polyethylene and nylon composite wires); elastic material such as elastic cloth or polyporous elastic cloth can also be used. In another embodiment, the tensile member 3 may be a metal wire, metal sheet, a carbon fiber thread, ligament line, non-elastic tension line, and non-elastic cloth, non-elastic polyporous cloth or combination thereof. This is not limited.

Figure 10:
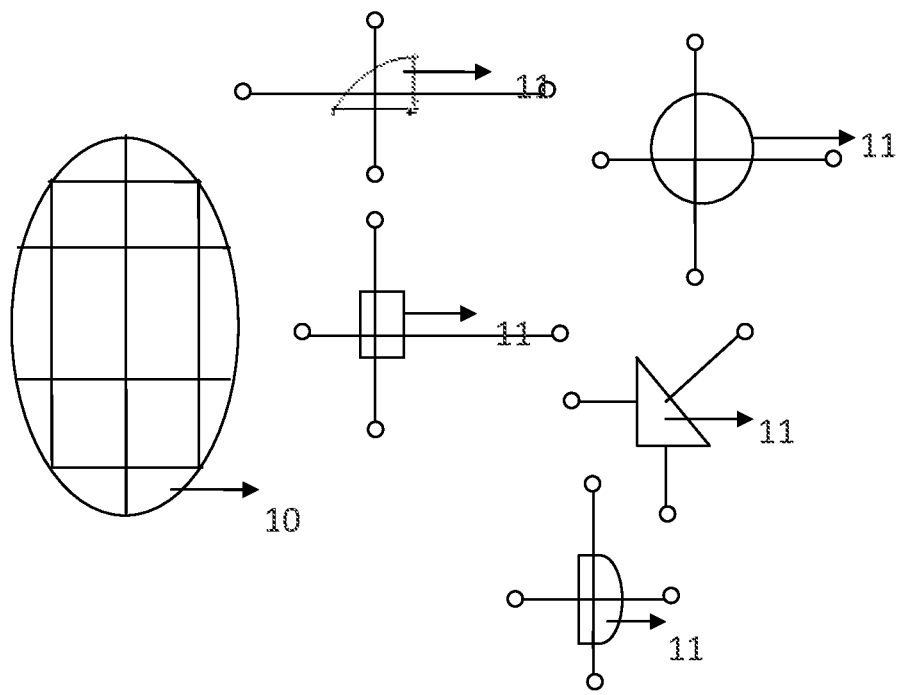
FIG. 10 is a schematic diagram of an embodiment of muscle prosthesis main body according to the invention.

In yet another embodiment as shown in FIG. 10, muscle prosthesis main body 10 is composed of multiple of muscle prosthesis units 11. Adjacent muscle prosthesis units 11 of muscle prosthesis 10 are connected together. Muscle prosthesis units 11 may be consisted of muscle prosthesis units 11 having different model, different shape, or same model, same shape. Each part in unit 11 is combined together with own pull wires, and is applied in acute repair surgeries. For example: after trauma or tumor resection soft tissue defects' immediate filling repairing.

In the present invention, the fixing member 1 could use one or more of anchor, tissue clip, and metal nail or screw and so on or a combination thereof, or other parts which are suited to connect and fix to human bones or tendons and fascia. This was not limited. Anchor, metal nail or screw etc. fasten tensile member 3 exposure outside the silica outer capsule 2 to body's natural muscle starting and ending points, which were replaced by muscle prosthesis, that is, to the bones, the number of anchors were determined by the size of the muscle and the part of the alternative, at least two.

In the present invention muscle prosthesis, the contour of the prosthesis fully simulated the shape of defects in patients. It allowed patients shape is in compliance better with physiological curve shape of human body. The tension wire knitting under contracted state is wrapped together by silicone outer capsule and forms suspension fixing system for prosthesis with combined anchor together, in order to fix better prosthesis to the human body. There are some patients whose joint could not fulfill its role because of missing or paralyzed joint muscles, at this time artificial muscle could be implanted and fixed cross joints. The artificial muscle maintains a certain tension by pull line, so that the joint could be fixed in a functional position, to recovery of function of muscles and joints in patients to greatest degree.

The present invention also provides a method of manufacturing muscle prosthesis. The method comprised: setting muscle prosthesis main body and suspension fixing device consisted of at least one stretching member and at least two fixing members; embedding the tensile members into the main body of the muscle prosthesis so that the tensile member can extend to the outside of the main body of the muscle prosthesis; connecting the fixing member to extending end of the tensile member, and fastening the muscle prosthesis to the skeletons of human body or muscle tendon and fascia of human body by the fixing members and the tensile members.

As a preferred embodiment of manufacturing method of the present invention, the muscle prosthesis main body includes a silicon outer capsule 2 and the filling part 4. The described method further includes: filling the filler 4 into the silicon outer bag 2 and being formed integrally with the silicon outer bag 2, the tensile members 3 is set as more than one tension wires 3, the tensile members 3 being laid on the initial surface of the silicon outer bag 2 in the longitudinal and transverse directions, longitudinal and transverse tensile members 3 are laid to run crookedly. The initial surface outer silicon capsule is coated repeatedly using the same material as that of the outer silicon capsule 2, so that the tensile members 3 and outer silicon capsules 2 being combined together, so that the tensile members 3 are embedded in the outer silicon capsules 2 and they together formed a net bag-like structure.

Furthermore, the tension wire 3 are set up to run along S shape in both longitudinal and transverse directions, each tension wire runs along S shape formed of two semicircle which is the same radius, and complies with the principle: be knotted at the intersections between the longitudinal and transverse tension wire 3, being disjoint between one longitudinal tension wire 3 and other longitudinal tension wires 3, being disjoint between one transverse tension wire 3 and other transverse tension wires 3.

Furthermore, the stretchable length of the silicon outer capsule 2 is one times of its nature length, and stretchable length of tension wire 3 can be less than three-fifths of stretchable length of the silicon outer capsule 2.

Figure 3:
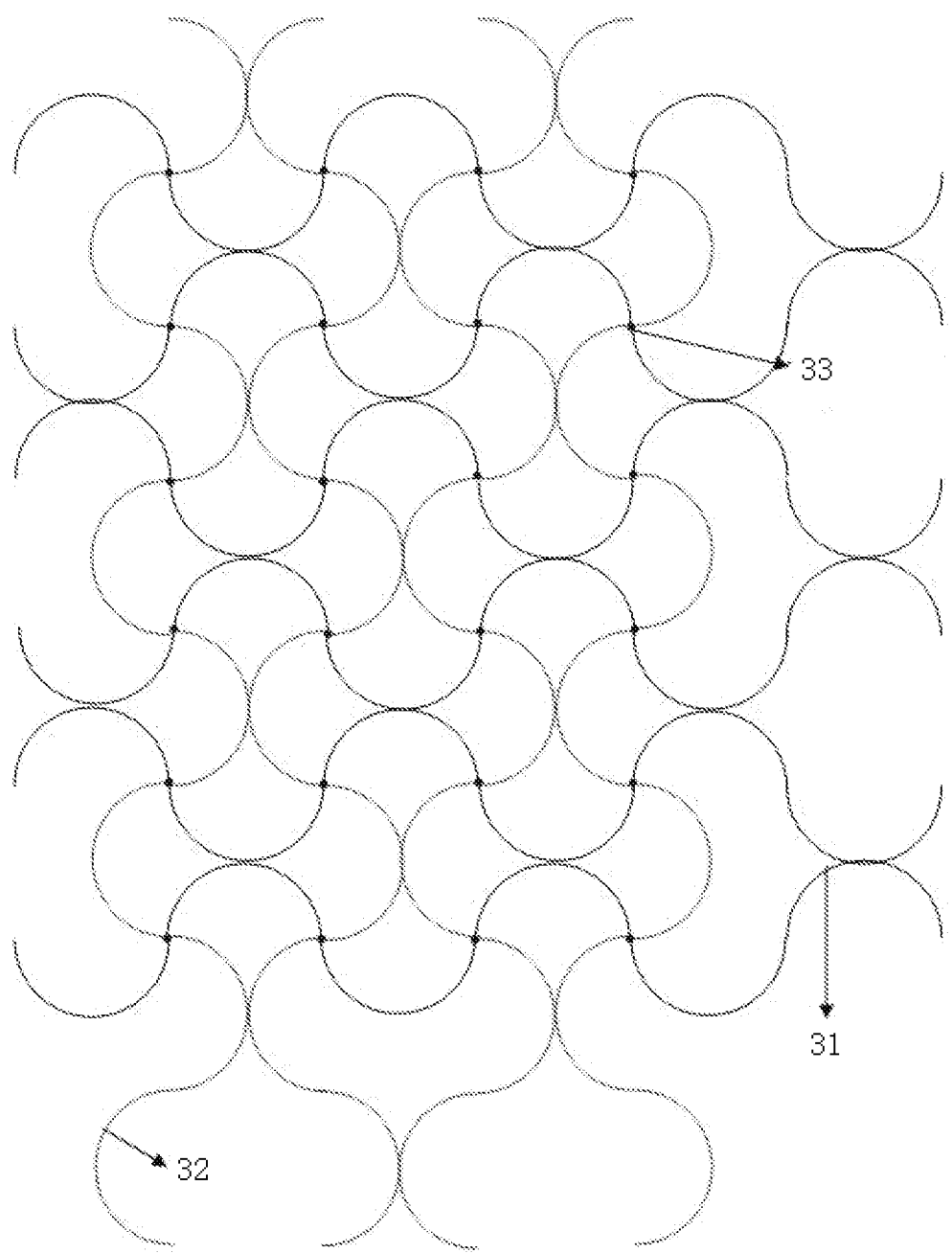
FIG. 3 is layout drawing of pull line according to the invention.

As a another preferred embodiment of manufacturing method of this invention, the method also comprises: the tensile members impenetrates the main body of the artificial muscle in the longitudinal and/or transverse direction and combine with the artificial muscle main body together; and the tensile members run along the straight line in the longitudinal and/or transverse direction; the fixing member is connected to the tensile member, so the suspension fixing device comprised of the fixing members and the tensile members can fasten the muscle prosthesis to the bone or human tendons and fascias As shown in FIG. 1, when a muscle prosthesis of this invention is applied to the quadriceps muscle; firstly, the lower limb of the patient is scanned by spiral CT in a thin layer, the two-dimensional CT scanned Dicom image data are input into the workstation respectively to conduct soft tissue reconstruction, and then, measure the reconstructed three-dimensional model with measuring software on the workstation, to determine the differences between the left leg and right leg of patient; therefore, determine the desired shape and volume of the artificial muscle. After the ratiometric conversion calculated, the patient needs to fill the longitudinal length of quadriceps muscle is approximately equal to L=400 mm, the lateral length is approximately equal to K=200 mm, the thickness is approximately equal to the shape of a rectangular parallelepiped of G=20 mm. Tension wire 3 formed a knitting which runs along S shape having two semicircle with radius R=2.5 mm, the knitting is wrapped by the silicone outer capsule 2, the filler 4 is filled into the silicon outer capsule 2 to form a integer; the tension wires 3 which is extended to outside of the silicon outer capsule 2 is fixed by the anchor nail 1 to the starting point: anterior inferior iliac spine, femoral body in front of the femur thick outer lip, medial femoral thick lips, and to the end: the tibial tuberosity. (Note: in the anatomy, the quadriceps muscle is composed of four muscles, including rectus femoris starts from the anterior inferior iliac spine; stocks muscle body starts from the front of the femur; vastus lateralis muscle starts from the lateral femoral thick lip; the vastus medialis starting from the medial femoral thick lips. At last, the heads of four muscles combined into a muscle tendon, surrounding the patella, form the tibial tuberosity end at the patellar tendon). Setting up 79 wires in the longitudinal direction and 87 wires in the transverse, the stretchable length of longitudinal direction can reach: max 228 mm and minimum 0 mm. Maximum lateral stretchable length can be 125.4 mm minimum 0 mm. The anchoring positions need 10 anchors: 2 for anterior inferior iliac spine, 2 for front of femoral body, 2 for femur thick lateral lips, 2 for medial femoral thick lip, and 2 for ends tibial tuberosity. And, between transverse tension wires 31 are disjoint and between longitudinal tension wires 32 are disjoint, but transverse tension wires 31 and longitudinal tension wires 32 intersects, as shown in FIG. 3. Of course, the numbers of tension wires and anchors required are different for different patients and the length L and other values also can be changed.

Figure 4:
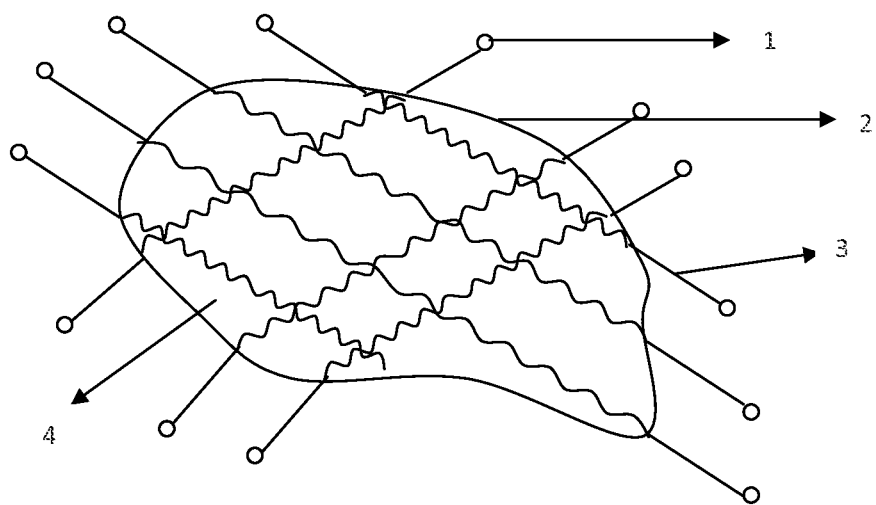
FIG. 4 is a schematic diagram of the muscle prosthesis for repairing temporalis according to the invention.

As shown in FIG. 4, when a artificial muscle of the invention is applied to the repairing of temporal muscle, designing the artificial muscle of the temporal muscle shape, size, shape and the thickness of which approximates to the shape of three-dimensional reconstruction after CT scanning of the patient. After implanting into temporal of the patient, adjusting the thickness and shape of the artificial muscle by tension wire 3 netted in the silicon outer capsule 2, from different angles and at different tensile strength to achieve the degree simulating the defected neutral muscle, then fixing tension wires 3 to the skull by the anchor nail 1. When repairing temporal muscle, usually two tension wires 3 and two anchor nails will be able to anchor the artificial muscle in correct place and can achieve the function of the defect muscle, wherein one of the tension wires 3 has a anchor nail and the other does not. Of course, the numbers of anchor nail and tension wire are determined based on the actually need of patient.

Figure 5:
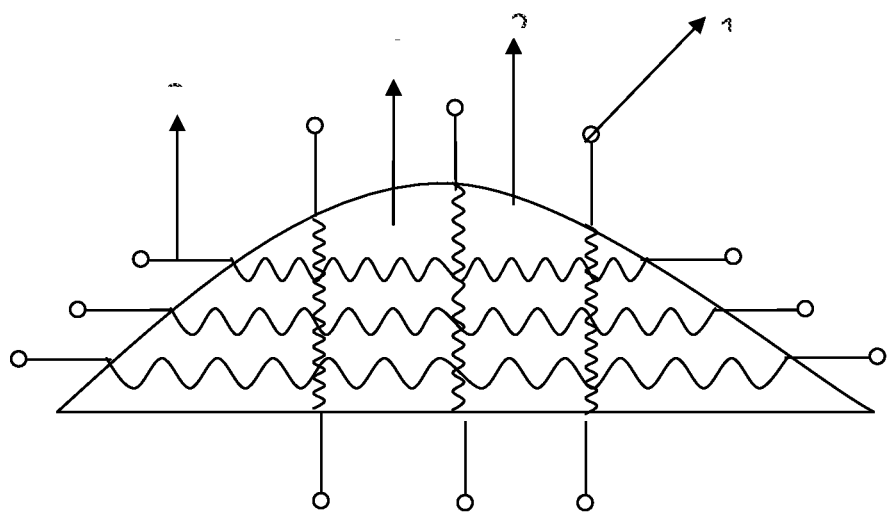
FIG. 5 is a schematic diagram of the vertex muscle prosthesis for muscle prosthesis implantation outside the skull to increase the height according to the invention.

As shown in FIG. 5, a artificial muscle of this invention is applied to muscle prosthesis implanted to the surface of skull to increase the height. Designing the artificial muscle shape on the surface of skull based on the needs of patient and after implanting the artificial muscle adjusting the thickness of the artificial muscle to suitable the patient's with degree by the tension wires 3 around artificial muscle on the head top, then fixing tension wires 3 to the skull by the anchor nail 1 to reach the aim of increasing the height. The numbers of anchor and tension wire are determined based on the anatomy of the muscle outside the skull, the number of anchor usually is six to eight and tension wire usually is four to six.

Figure 6:
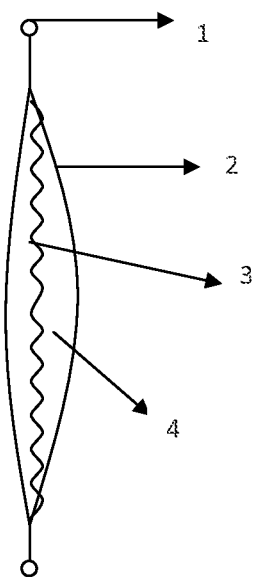
FIG. 6 is a schematic diagram of the muscle prosthesis for correcting mild to moderate bowleg according to the invention.

As shown in FIG. 6, a artificial muscle of this invention is applied to correct mild-to-moderate O-shaped legs. The shape of the artificial muscles is designed based on the gap between the two calves when the patient was upright position; after the artificial muscles implant, adjust the artificial muscle to the fit size, thickness, shape by tension wire 3 around the artificial muscles, and then fix the tension wire 3 to the tibia by anchor 1, to achieve the purpose of correcting the mild-to-moderate O-shaped legs. It is different from artificial muscle for repairing temporalis muscle and the muscle of surface skull, the artificial muscle which is used to correct O-shaped leg is in position having more activities, easy to occur shift and even tear, therefore, it usually needs dozens of tension wires and dozens of anchor nails to fix it in place.

Figure 7:
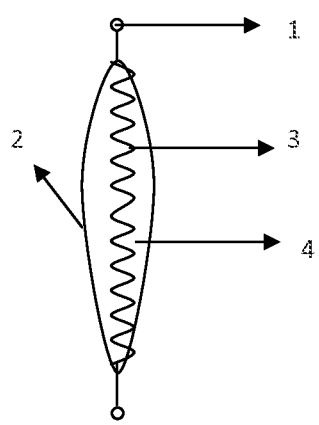
FIG. 7 is a schematic diagram of the muscle prosthesis for repairing the clawhand after nerve injury according to the invention.

As shown in FIG. 7, the muscle prosthesis of the invention is applied to repair ulnar nerve injury after claw hand. Design muscles prosthesis with different shapes based on the patient's interosseous muscle, lumbrical, thenar, hypothenar muscle sizes, implant the muscles prosthesis in the corresponding position, adjust the muscles prosthesis to suitable shape by tension wire 3 around the prosthesis, then fix tension wires to the finger bone, metacarpal bone and carpal bone, etc. Adjusting lumbrical longitudinal tension wire, can fix the metacarpophalangeal joints in the hand function position, effectively correcting the joint hyperextension and the claw hand deformity of the interphalangeal joint with flexion. Two transverse tension wire (one with anchor nail) and two longitudinal tension wire (one with two anchor nails) can fix the lumbrical muscle prosthesis in place.

As yet another preferred embodiment of manufacturing method of the present invention, the body of muscle prosthesis is solid silica gel, the solid silica gel body can be molded by injection molding, in the process of injection molding, the tensile members 3 are laid to impenetrate the solid silica gel body in longitudinal and/or lateral direction.

Technical personnel in the field can understand, the forgoing description of the invention to the muscle prosthesis implant can be used in manufacturing method of the muscles prosthesis implanted in human body described herein, accordingly, the description of muscles prosthesis manufacturing method of the present invention can also be applied to the muscles prosthesis described above, this is no longer the description herein.

Muscle prosthesis implant of the invention can be used to repair soft tissue defect in any areas of the body and congenital muscular dystrophy and filling after tumor resection, design different muscles prosthesis based on patient's defect size, thickness and shape in different parts, and adjust the muscles prosthesis to appropriate size, thickness and shape by the tension wires around the prosthesis, and then fix the tensile members on bone by fixing members to achieve the purpose of repairing tissue defect. It should be noted that in the drawings, the number of tensile member and fixing member is merely illustrative and is not limited to this. Technical personnel in the field can make various corresponding changes and modifications to the invention without departwent of the spirit of the invention, the corresponding changes and modifications fall in within the scope of the protection of claims of this invention.

The invention claimed is:

1. A muscle prosthesis with suspension fixing device for implantation in a human body, comprising: a muscle prosthesis body and suspension fixing device, said suspension fixing device comprising at least one tensile member and at least two fixing members, said tensile members embedded in said muscle prosthesis body and extending to outside of said muscle prosthesis body, said fixing members connecting to an extended end of said tensile member, said suspension fixing device fixing said muscle prosthesis to human bones or tendons and fascia, wherein said muscle prosthesis comprises a silicon outer bag and a filler, said filler filling in said silicon outer bag, said filler and said silicon outer bag formed integrally, said tensile member provided as a plurality of pulling wires, the plurality of pulling wires embedded within said silicon outer bag in both longitudinal and lateral directions and combined with said silicon outer bag together forming a net bag-like structure, said longitudinal and transverse directions pulling wires running crookedly; said fixing member connecting to tension wire, said suspension fixing device composed by said fixing members and tension wires fixing elastically said muscle prosthesis to a bone.

2. The muscle prosthesis according to claim 1, wherein said pulling wires run along an S shape in both longitudinal and transverse directions; each pulling wire forming a sigmoid curve having two semicircles with a same radius, and complying with such a principle: knotting at intersections between longitudinal and lateral tension wire, being disjoint between longitudinal tension wires, and being disjoint between lateral tension wires.

3. The muscle prosthesis according to claim 1, wherein said pulling wires run along a V shape curve in both longitudinal and transverse directions; and comply with such a principle: knotting at intersections between longitudinal and lateral tension wire, never contacting each other between longitudinal tension wires and never contacting each other between lateral tension wires.

4. The muscle prosthesis according to claim 1, wherein a stretchable length of said silicon outer bag is two times its natural length, and a stretchable length of the tension wire is less than three-fifths of the stretchable length of the silicon outer bag.

5. The muscle prosthesis according to claim 1, wherein said filler comprises high viscosity elastic silicone gel, boron body, or other soft materials suitable for implantation into the human body.

6. The muscle prosthesis according to claim 1, wherein said tension wire comprises ultrahigh molecular weight polyethylene and nylon composite wire or metal wire or a carbon fiber strand or ligament line.

7. The muscle prosthesis according to claim 1, wherein said muscle prosthesis body comprises a silicon outer bag and a filler, said filler filled in said silicon outer bag and formed integrally with said silicon outer bag, said tensile members penetrating said muscle prosthesis body in a longitudinal and/or transverse direction and combining together with said muscle prosthesis body and running along a straight line in the longitudinal and/or transverse direction, the suspension fixing device composed of said fixing members and said tensile members fasten said muscle prosthesis to a bone or human tendons and sinews membrane.

8. The muscle prosthesis according to claim 1, wherein said muscle prosthesis comprises a solid silicone body, said tensile members penetrating a solid silica gel in a longitudinal and/or transverse direction.

9. The muscle prosthesis according to claim 1, wherein said muscle prosthesis body is constituted by a plurality of adjacent muscle prosthesis units connected together.

10. A method for manufacturing a muscle prosthesis for implantation into human body, comprising:
   providing a muscle prosthesis body and a suspension fixing device composed of at least one tensile member and at least two fixing members,
   embedding one of said tensile members in the main body of said muscle prosthesis, and causing the tensile member to extend to outside of said muscle prosthesis body,
   connecting one of said fixing members to an extended end of said tensile member, fastening said muscle prosthesis to human skeleton or human tendons and fascia by said fixing members and said tensile members,
   wherein said muscle prosthesis body includes a silicon outer capsule and filler, the method further comprising:
      said filler filled into said silicon outer capsule and formed integrally with said silicon outer capsule;
      said tensile member set as a plurality of tension lines, said tension lines laid on an initial surface of said silicon outer capsule, and longitudinal and transverse tension lines laid to run crookedly, the initial surface of the silicon outer capsule coated repeatedly with the same material as a material of the silicon outer capsule, thus said tension lines and said outer silicone capsule combining together, so that the tension lines are buried in said silicon outer capsule, and form a net bag-like structure with said silicon outer capsule.

11. The method for a manufacturing muscle prosthesis according to claim 10, wherein said tensile lines are laid to run along an S shape in both longitudinal and transverse directions, each tension line laid to run along the S shape having two semicircles with a same radius, and complying with such a principle: knotting at intersections between longitudinal and lateral tension wires, never contacting each other between longitudinal tension wires, and never contacting each other between lateral tension wires.

12. The method for manufacturing a muscle prosthesis according to claim 10, wherein pull lines are laid to run along a V shape in both longitudinal and transverse directions; and complying with such a principle: knotting at intersections between longitudinal and lateral tension wires, never contacting each other between longitudinal tension wires and never contacting each other between lateral tension wires.

13. The method for manufacturing a muscle prosthesis according to claim 10, wherein a stretchable length of said silicon outer capsule is two times its natural length, and a stretchable length of said tension line is less than three-fifths of the stretchable length of the silicon outer capsule.

14. The method for manufacturing a muscle prosthesis according to claim 10, wherein said muscle prosthesis body includes a silicon outer bag and filler, the method further comprising:
   said filler filled into said silicon outer bag and formed integrally with said silicon outer bag;
   said tensile members impenetrating said muscle prosthesis in the longitudinal and/or transverse direction and combining with said muscle prosthesis body together, and the longitudinal and/or transverse tensile members running linearly; said fixing member connected to said tensile member, said suspension fixing device composed of said fixing members, and wherein said tensile members fasten said muscle prosthesis to a bone or human tendons and fascia.

15. The method for manufacturing a muscle prosthesis according to claim 10, wherein said muscle prosthesis body is a solid silica gel body, the method further comprising:
   said muscle prosthesis body molded by injection molding as a solid silica gel body;
   said tensile members laid to impenetrate said solid silica gel body in longitudinal and/or transverse directions during the process of said injection molding.

* * * * *